(12) United States Patent
Yegnasubramanian et al.

(10) Patent No.: US 9,297,806 B2
(45) Date of Patent: Mar. 29, 2016

(54) 5-HYDROXYMETHYLCYTOSINE IN HUMAN CANCER

(71) Applicant: The Johns Hopkins University, Baltimore, MD (US)

(72) Inventors: Srinivasan Yegnasubramanian, Perry Hall, MD (US); Michael Christoph Haffner, Baltimore, MD (US); Alcides Chaux, Baltimore, MD (US); William G. Nelson, Towson, MD (US); Angelo M. DeMarzo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 8 days.

(21) Appl. No.: 13/956,879

(22) Filed: Aug. 1, 2013

(65) Prior Publication Data

US 2014/0038183 A1    Feb. 6, 2014

Related U.S. Application Data

(60) Provisional application No. 61/678,237, filed on Aug. 1, 2012.

(51) Int. Cl.
*G01N 33/53* (2006.01)
*G01N 33/574* (2006.01)

(52) U.S. Cl.
CPC ...... *G01N 33/57496* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,545,806 A | 8/1996 | Lonberg | |
| 5,545,807 A | 8/1996 | Surani | |
| 5,569,825 A | 10/1996 | Lonberg | |
| 5,625,126 A | 4/1997 | Lonberg | |
| 5,633,425 A | 5/1997 | Lonberg | |
| 5,641,870 A | 6/1997 | Rinderknecht | |
| 5,661,016 A | 8/1997 | Lonberg | |
| 5,750,373 A | 5/1998 | Garrard | |
| 2009/0202977 A1* | 8/2009 | Ott et al. | 435/1.2 |
| 2011/0236894 A1 | 9/2011 | Rao | |
| 2011/0301045 A1 | 12/2011 | He | |

FOREIGN PATENT DOCUMENTS

| WO | 2010037001 A2 | 4/2010 |
|---|---|---|
| WO | 2011127136 A1 | 10/2011 |

OTHER PUBLICATIONS

Jin et al. (Cancer Res 2011 vol. 71, p. 7360-5).*
Ko et al. (Nature 2010 vol. 468, p. 839-843).*
Globisch et al. (PlusOne 2010 vol. 5, e15367, 9 pages).*
Tahiliani, et al (2009) Conversion of 5-methylcytosine to 5-hydroxymethylcytosine in mammalian DNA by MLL partner TET1. Science 324:930-935.
Wu, et al (2011) Dual functions of Tet1 in transcriptional regulation in mouse embryonic stem cells. Nature 473:389-393.
Pastor, et al (2011) Genome-wide mapping of 5-hydroxymethylcytosine in embryonic stem cells. Nature 473:394-397.
Reik, (2007) Stability and flexibility of epigenetic gene regulation in mammalian development. Nature 447:425-432.
Chen, et al (2011) DNA methylation and demethylation in mammals. J Biol Chem 286:18347-18353.
Esteller (2008) Epigenetics in cancer. N Engl J Med 358:1148-1159.
Jones et al (2007) The epigenomics of cancer. Cell 128:683-692.
Jones et al (2009) Rethinking how DNA methylation patterns are maintained. Nat Rev Genet 10:805-811.
Ooi et al (2008) The colorful history of active DNA demethylation. Cell 133:1145-1148.
Wyatt et al (1953) The bases of the nucleic acids of some bacterial and animal viruses: the occurrence of 5-hydroxymethylcytosine. Biochem J 55:774-782.
Kothari et al (1976) 5-Methylcytosine content in the vertebrate deoxyribonucleic acids: species specificity. J Mol Evol 7:325-329.
Penn et al (1976) Modification of brain deoxyribonucleic acid base content with maturation in normal and malnourished rats. Biochem J 155:709-712.
Penn et al (1972) The presence of 5-hydroxymethylcytosine in animal deoxyribonucleic acid. Biochem J 126:781-790.
Kriaucionis, et al (2009) The nuclear DNA base 5-hydroxymethylcytosine is present in Purkinje neurons and the brain. Science 324:929-930.
Iqbal, et al (2011) Reprogramming of the paternal genome upon fertilization involves genome-wide oxidation of 5-methylcytosine. Proc Natl Acad Sci U S A 108:3642-3647.
Xu et al (2011) Genome-wide regulation of 5hmC, 5mC, and gene expression by Tet1 hydroxylase in mouse embryonic stem cells. Mol Cell 42:451-464.
Wu et al (2011) Genome-wide analysis of 5-hydroxymethylcytosine distribution reveals its dual function in transcriptional regulation in mouse embryonic stem cells. Genes Dev 25:679-684.
Stroud et al (2011) 5-Hydroxymethylcytosine is associated with enhancers and gene bodies in human embryonic stem cells. Genome Biol 12:R54.
Robertson et al (2011) The presence of 5-hydroxymethylcytosine at the gene promoter and not in the gene body negatively regulates gene expression. Biochem Biophys Res Commun 411:40-43.
Fica et al (2011) Dynamic regulation of 5-hydroxymethylcytosine in mouse ES cells and during differentiation. Nature 473:398-402.

(Continued)

*Primary Examiner* — Jacob Cheu
(74) *Attorney, Agent, or Firm* — Johns Hopkins Technology Transfer

(57) ABSTRACT

The present invention relates to the field of cancer. More specifically, the present invention provides methods and compositions useful for diagnosing or predicting cancer in a patient. In one embodiment, a method for identifying a patient as having cancer comprises the steps of (a) providing a formalin-fixed, paraffin-embedded or fresh frozen sample of patient tissue; (b) steaming the sample in antigen retrieval buffer; (c) incubating the sample in hydrochloric acid (HCl); (d) incubating the sample with an affinity reagent specific for 5hmC under conditions to form a complex between the affinity reagent and 5-hydroxymethylcytosine (5hmC) present in the sample; (e) detecting the complexes formed between 5hmC and the affinity reagent with secondary detection reagents; (f) quantifying 5hmC levels; and (g) identifying the patient as having cancer if the 5hmC levels in the sample are reduced as compared to a control.

8 Claims, 11 Drawing Sheets

(56) References Cited

OTHER PUBLICATIONS

Williams et al (2011) TET1 and hydroxymethylcytosine in transcription and DNA methylation fidelity. Nature 473:343-348.
Globisch et al (2011) Tissue distribution of 5-hydroxymethylcytosine and search for active demethylation intermediates. PLoS One 5:e15367.
Sfanos et al (2011) Identification of replication competent murine gammaretroviruses in commonly used prostate cancer cell lines. PLoS One 6:e20874.
Ito et al (2010) Role of Tet proteins in 5mC to 5hmC conversion, ES-cell self-renewal and inner cell mass specification. Nature 466:1129-1133.
Song et al (2011) Selective chemical labeling reveals the genome-wide distribution of 5-hydroxymethylcytosine. Nat Biotechnol 29:68-72.
Ruzov et al (2011) Lineage-specific distribution of high levels of genomic 5-hydroxymethylcytosine in mammalian development. Cell Res 21:1322-1342.
Vanderflier, et al (2009) Stem cells, self-renewal, and differentiation in the intestinal epithelium. Annu Rev Physiol 71:241-260.
Barker et al (2007) Identification of stem cells in small intestine and colon by marker gene Lgr5. Nature 449:1003-1007.
Civin (2010) CD34 stem cell stories and lessons from the CD34 wars: the Landsteiner Lecture 2009. Transfusion 50:2046-2056.
Ratajczak (2008) Phenotypic and functional characterization of hematopoietic stem cells. Curr Opin Hematol 15:293-300.
Gerber et al (2010) Characterization of chronic myeloid leukemia stem cells. Am J Hematol 86:31-37.
Demarzo et al (2010) Prostate cancer: New answers prompt new questions regarding cell of origin. Nat Rev Urol 7:650-652.
Nelson et al (2009) Epigenetic alterations in human prostate cancers. Endocrinology 150:3991-4002.
English et al (1987) Response of glandular versus basal rat ventral prostatic epithelial cells to androgen withdrawal and replacement. Prostate 11:229-242.
Garraway et al (2010) Human prostate sphere-forming cells represent a subset of basal epithelial cells capable of glandular regeneration in vivo. Prostate 70:491-501.
Petersen et al (2010) Stem cells in the human breast. Cold Spring Harb Perspect Biol 2:a003160.
Yegnasubramanian et al (2008) DNA hypomethylation arises later in prostate cancer progression than CpG island hypermethylation and contributes to metastatic tumor heterogeneity. Cancer Res 68:8954-8967.
Valinluch et al (2004) Oxidative damage to methyl-CpG sequences inhibits the binding of the methyl-CpG binding domain (MBD) of methyl-CpG binding protein 2 (MeCP2). Nucleic Acids Res 32:4100-4108.
Jin et al (2010) Examination of the specificity of DNA methylation profiling techniques towards 5-methylcytosine and 5-hydroxymethylcytosine. Nucleic Acids Res 38:e125.
Frauer et al (2011) Recognition of 5-hydroxymethylcytosine by the Uhrf1 SRA domain. PLoS One 6:e21306.
Valinluck et al (2007) Endogenous cytosine damage products alter the site selectivity of human DNA maintenance methyltransferase DNMT1. Cancer Res 67:946-950.
Guo et al (2011) Hydroxylation of 5-methylcytosine by TET1 promotes active DNA demethylation in the adult brain. Cell 145:423-434.
Cortellino et al (2011) Thymine DNA glycosylase is essential for active DNA demethylation by linked deamination-base excision repair. Cell 146:67-79.
Ko et al (2010) Impaired hydroxylation of 5-methylcytosine in myeloid cancers with mutant TET2. Nature 468:839-843.
Konstandin et al (2011) Genomic 5-hydroxymethylcytosine levels correlate with TET2 mutations and a distinct global gene expression pattern in secondary acute myeloid leukemia. Leukemia 25:1649-1652.
Wood et al (2007) The genomic landscapes of human breast and colorectal cancers. Science 318:1108-1113.
Sjoblom et al (2006) The consensus coding sequences of human breast and colorectal cancers. Science 314:268-274.
Kan et al (2010) Diverse somatic mutation patterns and pathway alterations in human cancers. Nature 466:869-873.
Berger et al (2011) The genomic complexity of primary human prostate cancer. Nature 470:214-220.
Figueroa et al (2010) Leukemic IDH1 and IDH2 mutations result in a hypermethylation phenotype, disrupt TET2 function, and impair hematopoietic differentiation. Cancer Cell 18:553-567.
Xu et al (2011) Oncometabolite 2-hydroxyglutarate is a competitive inhibitor of α-ketoglutarate-dependent dioxygenases. Cancer Cell 19:17-30.
Jackson et al (2004) DNA hypomethylation is prevalent even in low-grade breast cancers. Cancer Biol Ther 3:1225-1231.
Sunami et al (2011) Line-1 hypomethylation during primary colon cancer progression. PLoS One 6:e18884.
Haffner et al (2011) Global 5-hydroxymethylcytosine content is significantly reduced in tissue stem/progenitor cell compartments and in human cancers. Oncotarget 2:627-637.
Jin et al (2011) 5-Hydroxymethylcytosine is strongly depleted in human cancers but its levels do not correlate with IDH1 mutations. Cancer Res 71:7360-7365.
Acevedo et al (2011) Novel DNA binding domain-based assays for detection of methylated and nonmethylated DNA. Epigenomics 3:93-101.
Li et al (2011) Distribution of 5-hydroxymethylcytosine in different human tissues. J Nucleic Acids 2011:870726.
Yegnasubramanian et al (2006) Combination of methylated-DNA precipitation and methylation-sensitive restriction enzymes (Compare-MS) for the rapid, sensitive and quantitative detection of DNA methylation. Nucl Acids Res 34:e19.
Kohler et al (1975) Continuous cultures of fused cells secreting antibody of predefined specificity. Nature 256:495-497.
McCafferty et al (1990) Phage antibodies: filamentous phage displaying antibody variable domains. Nature 348:552-554.
Clackson et al (1991) Making antibody fragments using phage display libraries. Nature 352:624-628.
Marks et al (1991) By-passing immunization. Human antibodies from V-gene libraries displayed on phage. J Mol Biol 222:581-597.
Jones et al (1986) Replacing the complementarity-determining regions in a human antibody with those from a mouse. Nature 321:522-525.
Riechmann et al (1988) Reshaping human antibodies for therapy. Nature 332:323-327.
Boemer et al (1991) Production of antigen-specific human monoclonal antibodies from in vitro-primed human splenocytes. J Immunol 147:86-95.
Brennan et al (1985) Preparation of bispecific antibodies by chemical recombination of monoclonal immunoglobulin G1 fragments. Science 229:81-83.
Sheets et al (1998) Efficient construction of a large nonimmune phage antibody library: the production of high-affinity human single-chain antibodies to protein antigens. Proc Natl Acad Sci U S A 95:6157-6162.
Hoogenboom et al (1991) By-passing immunisation. Human antibodies from synthetic repertoires of germline VH gene segments rearranged in vitro. J Mol Biol 227:381-388.
Morimoto et al (1993) Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24:107-117.
Hedrick et al (1989) Use of keratin 903 as an adjunct in the diagnosis of prostate carcinoma. Am J Surg Pathol 13:389-396.
Verhoeyen et al (1988) Reshaping human antibodies: grafting an antilysozyme activity. Science 239:1534-1536.

\* cited by examiner

5-HYDROXYMETHYLCYTOSINE IN HUMAN CANCER

CROSS-REFERENCE TO RELATED APPLICATIONS

This application claims the benefit of U.S. Provisional Application No. 61/678,237, filed Aug. 1, 2012; which is incorporated herein by reference in its entirety.

STATEMENT OF GOVERNMENTAL INTEREST

This invention was made with government support under grant no. CA058236 and grant no. CA070196 awarded by NIH. The government has certain rights in the invention.

FIELD OF THE INVENTION

The present invention relates to the field of cancer. More specifically, the present invention provides methods and compositions useful for diagnosing or predicting cancer in a patient.

BACKGROUND OF THE INVENTION

Epigenetic modifications play a crucial role in cellular differentiation and have been implicated in numerous disease states including cancer. One of the most studied of these modifications is the addition of a methyl group on the 5-position of the cytosine (5mC) base in a CpG dinucleotide. Accumulation of methylation marks in CpG rich regions around the transcriptional start site of genes has been shown to be associated with alterations in chromatin organization ultimately leading to changes in locus specific transcriptional activity. Paradoxically, DNA methylation marks can be heritably maintained across cell division but can also be reversibly/dynamically altered to establish new epigenetic programs. However, major uncertainties remain on how cells can erase existing methylation marks.

The recent discovery of a group of enzymes of the ten-eleven translocated (TET) family that can specifically modify these DNA methylation marks by oxidizing 5-methylcytosine (5mC) to 5-hydroxymethylcytosine (5hmC) has added another dimension of complexity to our understanding of DNA methylation. It has been well established for decades that certain bacteriophages contain 5-hydroxymethylcytosine rather than cytosine in their genome to protect themselves from host-controlled nucleases. The presence of 5hmC in mammalian cells has historically been very controversial, and its role in mammalian genomes is not well understood. Interestingly, Penn et al. demonstrated in 1972 that 5hmC can be detected by crude chromatography methods in rodent brain and liver DNA preparations. More recently, using mass spectrometry, Kriaucionis and Heintz provided firm evidence for the presence of 5hmC in Purkinje cells of the murine cerebellum. Subsequently, several studies have addressed the potential role of 5hmC and the oxidizing enzymes of the TET protein family in genome organization and differentiation of murine embryonic stem (ES) cells. The tissue specific cellular distribution of 5hmC in normal adult tissues and neoplasia, however, has thus far not been well documented.

SUMMARY OF THE INVENTION

The present invention is based, at least in part, on the discovery of a global and profound cancer specific loss of 5-methylhydroxycytosine (5hmC) in prostate, breast and colorectal cancer. DNA methylation at the 5-position of cytosines (5mC) represents an important epigenetic modification involved in tissue differentiation and is frequently altered in cancer. Recent evidence suggests that 5mC can be converted to 5-hydroxymethylcytosine (5hmC) in an enzymatic process involving members of the TET protein family. Such 5hmC modifications are known to be prevalent in DNA of embryonic stem cells and in the brain, but the distribution of 5hmC in the majority of embryonic and adult tissues has not been rigorously explored. Here, we describe an immunohistochemical detection method for 5hmC and the application of this technique to study the distribution of 5hmC in a large set of mouse and human tissues. We found that 5hmC was abundant in the majority of embryonic and adult tissues. Additionally, the level of 5hmC closely tracked with the differentiation state of cells in hierarchically organized tissues. The highest 5hmC levels were observed in terminally differentiated cells, while less differentiated tissue stem/progenitor cell compartments had very low 5hmC levels. Furthermore, 5hmC levels were profoundly reduced in carcinoma of the prostate, breast and colon compared to normal tissues. Our findings suggest a distinct role for 5hmC in tissue differentiation, and provide evidence for its large-scale loss in cancers.

Accordingly, in one aspect, the present invention provides methods for diagnosing cancer in a patient. In one embodiment, a method for identifying a patient as having cancer comprises the steps of (a) providing a formalin-fixed, paraffin-embedded or fresh frozen sample of patient tissue; (b) steaming the sample in antigen retrieval buffer; (c) incubating the sample in hydrochloric acid (HCl); (d) incubating the sample with an affinity reagent specific for 5hmC under conditions to form a complex between the affinity reagent and 5-hydroxymethylcytosine (5hmC) present in the sample; (e) detecting the complexes formed between 5hmC and the affinity reagent with secondary detection reagents; (f) quantifying 5hmC levels; and (g) identifying the patient as having cancer if the 5hmC levels in the sample are reduced as compared to a control.

In certain embodiments, the patient sample is from any tissue with a suspected neoplastic growth (cancer). This includes solid tumors (including, but not limited to, prostate, breast, colon) as well as liquid tumors including, but not limited to, leukemia. In a specific embodiment, the quantifying step is accomplished by semi-quantitative scoring or by using an image analysis software program.

The present invention also provides a method for identifying a patient as having cancer comprising the steps of (a) labeling 5hmC in a patient tissue sample; (b) quantifying 5hmC levels; and (c) identifying the patient has having cancer if the 5hmC level is reduced relative to a control. In a specific embodiment, the labeling step comprises binding 5hmC with an affinity reagent. In another specific embodiment, the labeling step comprises an antigen retrieval step. In a more specific embodiment, the antigen retrieval step comprises steaming in antigen retrieval buffer and incubating in HCl. In particular embodiments, the patient sample is from tissue with suspected neoplastic growth. In certain embodiments, the patient tissue sample is a native, formalin-fixed, paraffin-embedded sample or a fresh frozen sample.

In a further embodiment, the present invention provides a method for diagnosing cancer or risk thereof in a patient comprising the steps of (a) performing an antigen retrieval step on native, formalin-fixed, paraffin-embedded tissue sample or a fresh frozen tissue sample from the patient; (b) labeling 5hmC present in the sample; (c) quantifying the levels of 5hmC in the sample; and (d) identifying the patient as having cancer or a risk thereof if the levels of 5hmC are reduced relative to a control from normal tissue. In certain embodiments, the sample is obtained from a lesion in the patient. In other embodiments, the antigen retrieval step comprises steaming in an antigen retrieval buffer and incubating in HCl. The patient sample can be from tissue with suspected neoplastic growth.

In a more specific embodiment, a method for identifying a patient as having cancer comprises the steps of (a) providing a formalin-fixed, paraffin-embedded sample of patient tissue; (b) steaming the sample in citrate buffer; (c) incubating the sample in hydrochloric acid (HCl); (d) immunolabeling 5-hydroxymethylcytosine (5-hmC) with an antibody; (e) detecting the immunocomplexes formed between 5-hmC and the antibody; (f) quantifying 5-hmC levels; and (g) identifying the patient as having cancer if the 5-hmC levels in the sample are reduced as compared to a control. In some embodiments, patient tissue is from the prostate, breast or colon. In a specific embodiment, the detection step comprises labeling the immunocomplexes with secondary antibodies conjugated with a fluorescent dye and visualizing using a fluorescence microscope. In another specific embodiment, the quantifying step is accomplished using an image analysis software program.

The present invention also provides a method for identifying a patient as having cancer comprising the steps of (a) immunohistochemically staining for 5-hmC in a patient tissue sample; (b) quantifying 5-hmC levels; and (c) identifying the patient has having cancer if the 5-hmC level is reduced relative to a control. In certain embodiments, the immunohistochemical staining step comprises an antigen retrieval step. In a more specific embodiment, the antigen retrieval step comprises steaming in citrate buffer and incubating in HCl. In particular embodiments, the patient tissue sample is from the prostate, breast or colon. In yet another embodiment, the patient tissue sample is formalin-fixed, paraffin-embedded.

In one embodiment, a method for diagnosing cancer or risk thereof in a patient comprises the steps of (a) performing an antigen retrieval step on a formalin-fixed, paraffin-embedded tissue sample from the patient; (b) immunohistochemically staining for 5-hmC; and (c) identifying the patient as having cancer or a risk thereof if the levels of 5-hmC are reduced relative to a control from normal tissue. In a specific embodiment, the sample is obtained from a lesion in the patient. In another specific embodiment, the antigen retrieval step comprises steaming in citrate buffer and incubating in HCl. In other embodiments, the patient tissue sample is from the prostate, breast or colon.

DETAILED DESCRIPTION OF THE INVENTION

Figure 1:
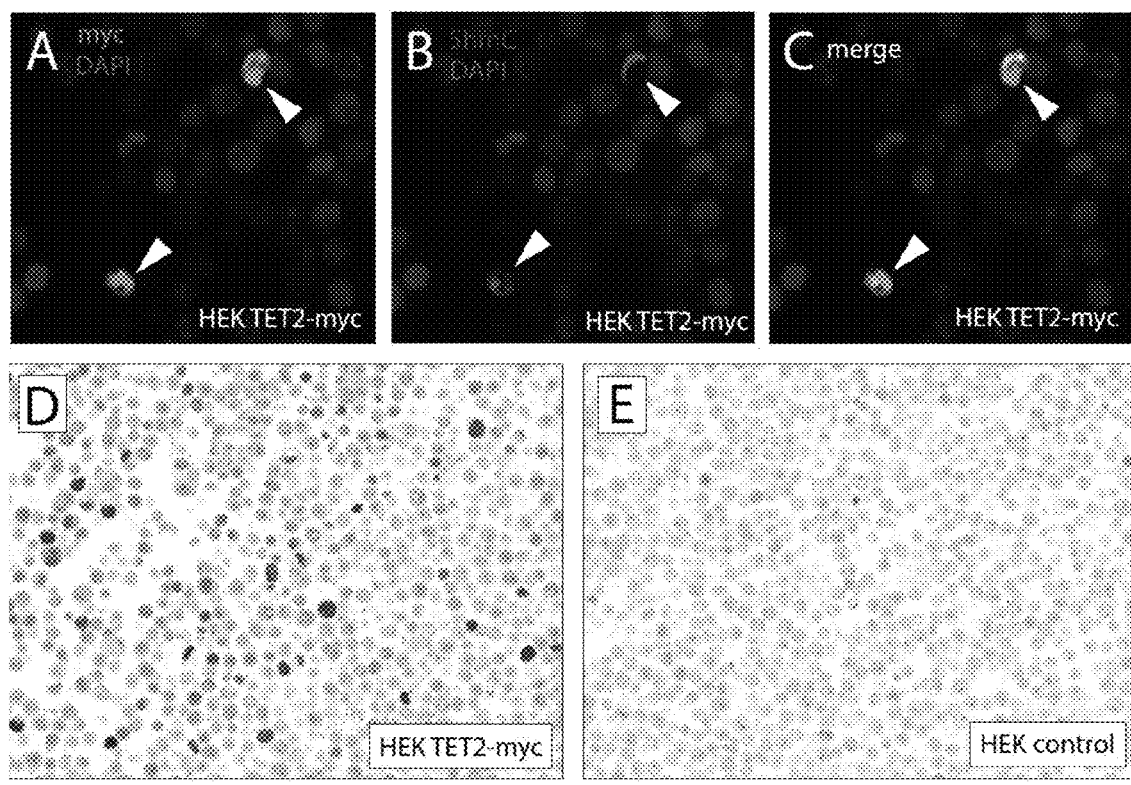
FIG. 1: Specificity of immunohistochemical detection of 5hmC. To assess the specificity of 5hmC immunolabeling of formalin-fixed paraffin-embedded cells, HEK293 cells were transfected with expression plasmids encoding for myc-tagged TET2 or control. Cell pellets were fixed and embedded in paraffin. Sections of the resulting paraffin block were co-immunolabeled with anti-myc and anti-5hmC specific antibodies and visualized using fluorophore conjugated secondary antibodies (A, B, C). Note that only cells that express high levels of TET2 (indicated by arrowheads) showed strong staining for 5hmC. (D, E) To show that 5hmC can be specifically detected using a chromogenic immunohistochemistry method, HEK293 cells overexpressing TET2-myd and HEK293 control cells(E) were stained with 5hmC specific antibodies and immunocomplexes were visualized using HRP conjugated secondary antibodies with DAB as a chromogen.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

We applied a novel immunohistochemical staining method to detect 5hmC in a variety of normal murine and human tissues. Interestingly, we found that in embryonic and adult tissues, the abundance of 5hmC correlates with cellular differentiation, with more differentiated cells showing higher 5hmC staining. Furthermore, we observed an almost uniform loss of 5hmC levels in cancer tissues as compared to their normal counterparts, suggesting a complex and yet to be defined role of 5hmC in tissue differentiation and neoplasia. Accordingly, 5hmC could be used as a specific marker for precancerous lesions and invasive cancers and could help to guide diagnostic decision making. Indeed, with these methods, 5hmC can easily be detected in standard tissue sections currently used for cancer diagnosis. The differences in 5hmC levels between normal tissues and cancers are so profound that the absence of 5hmC can specifically mark neoplastic or pre-neoplastic lesions. Therefore, we think that this mark might be helpful in the diagnosis of malignant tumors and could easily be integrated in the standard pathology diagnosis pipeline.

I. Definitions

A "significant" decrease in a value, as used herein, can refer to a difference which is reproducible or statistically significant, as determined using statistical methods that are appropriate and well-known in the art, generally with a probability value of less than five percent chance of the change being due to random variation. In general, a statistically significant value is at least two standard deviations from the value in a "normal" healthy control subject. Suitable statistical tests will be evident to a skilled worker. For example, a significant decrease in the amount of a biomarker compared to a baseline value (e.g., a control) can be about 50%, 2-fold, or higher. A significantly reduced amount of a biomarker of the invention compared to a suitable baseline value or control, then, is indicative that a patient has cancer (indicates that the subject is likely to have cancer). A subject is "likely" to have cancer if the subject has levels of the biomarker significantly below those of a healthy control or his own baseline (taken at an earlier time point or at the same time in a non-cancerous tissue or portion of the same tissue). In certain embodiments, the extent of the decreased levels correlates to the % chance. For example, the subject can have greater than about a 50% chance, e.g., greater than about 70%, 80% 90%, 95% or higher chance, of having cancer. In general, the presence of a reduced amount of a biomarker of the present invention is a strong indication that the subject has cancer or is likely to develop cancer.

As used herein, a "baseline value" generally refers to the level (amount) of a protein in a comparable sample (e.g., from the same type of tissue as the tested tissue), from a "normal" healthy subject that does not exhibit myocardial ischemia. If desired, a pool or population of the same tissues from normal subjects can be used, and the baseline value can be an average or mean of the measurements. Suitable baseline values can be determined by those of skill in the art without undue experimentation. Suitable baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of cancer.

Various methodologies of the instant invention include a step that involves comparing a value, level, feature, characteristic, property, etc. to a "suitable control," referred to interchangeably herein as an "appropriate control," a "baseline value" or a "control sample." A "suitable control," "appropriate control," a "baseline value" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or subject, e.g., a control or normal cell, organ, or subject, exhibiting, for example, normal traits. For example, the biomarkers of the present invention may be assayed for their 5hmC level in a sample from an unaffected individual (UI) or a normal control individual (NC) (both terms are used interchangeably herein). In another embodiment, a "suitable control" "appropriate control" or "baseline value" is a value, level, feature, characteristic, property, etc. determined prior to performing a therapy (e.g., a cancer treatment) on a subject. In yet another embodiment, a 5hmC level can be determined prior to, during, or after administering a therapy into a cell, organ, or subject. In a further embodiment, a "suitable control," "appropriate control" or a "baseline value" is a predefined value, level, feature, characteristic, property, etc. A "suitable control" can be a 5hmC profile that correlates to cancer, to which a subject sample can be compared. The patient sample can also be compared to a negative control, i.e., a 5hmC profile that correlates to not at risk of developing cancer.

The terms "subject," "individual," or "patient" are used interchangeably herein, and refer to a mammal, particularly, a human. The subject may have mild, intermediate or severe disease. The subject may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "sample," "subject sample," "biological sample," and the like, encompass a variety of sample types obtained from a patient, individual, or subject and can be used in a diagnostic or monitoring assay. The subject sample may be obtained from a healthy subject, a subject suspected to be at risk for cancer (e.g., family history) or a subject having a conditions associated with cancer. Moreover, a sample obtained from a subject can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a standard tissue sample taken for pathological analysis. In another embodiment, the sample is a formalin-fixed, paraffin-embedded tissue sample. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. In particular embodiments, samples comprise native, fresh-frozen and/or formalin-fixed, paraffin-embedded tissue blocks, such as blocks prepared from clinical or pathological biopsies, prepared for pathological analysis or study by immunohistochemistry.

An "affinity reagent" refers to biological molecules (antibody, aptamer, lectin, sequence-specific binding peptide/protein, etc.) that specifically bind with respective target molecules (e.g., 5hmC). In specific embodiments, an affinity reagent comprises an antibody. In other embodiments, an affinity reagent comprises an aptamer. In further embodiments, an affinity reagent comprises a protein (e.g., a recombinant protein) that specifically binds 5hmC. See Yegnasubramanian et al., 34(3) NUCL. ACIDS. RES. e19 (2006).

The terms "specifically binds to," "specific for," and related grammatical variants refer to that binding which occurs between such paired species as antibody/antigen, aptamer/target, enzyme/substrate, receptor/agonist and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, in certain embodiments, "specific binding" occurs between a paired species where there is interaction between the two which produces a bound complex having the characteristics of, for example, an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. In certain embodiments, the term refers to a molecule (e.g., an aptamer) that binds to a target (e.g., a protein) with at least five-fold greater affinity as compared to any non-targets, e.g., at least 10-, 20-, 50-, or 100-fold greater affinity.

The term "immunohistochemical" or as abbreviated "IHC" as used herein refer to the process of detecting antigens (e.g., 5hmC) in a biological sample by exploiting the binding properties of affinity reagents (e.g., antibodies) to antigens in the biologic sample.

The term "immunoassay" refers to a test that uses the binding of antibodies to antigens to identify and measure certain substances Immunoassays often are used to diagnose disease, and test results can provide information about a disease that may help in planning treatment. An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity.

The term "antibody" means an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE, etc.

The term "antibody fragment" refers to any derivative or portion of an antibody that is less than full-length. In one aspect, the antibody fragment retains at least a significant portion of the full-length antibody's specific binding ability, specifically, as a binding partner. Examples of antibody fragments include, but are not limited to, Fab, Fab', F(ab')2, scFv, Fv, dsFv diabody, and Fd fragments. The antibody fragment may be produced by any means. For example, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may comprise a single chain antibody fragment. In another embodiment, the fragment may comprise multiple chains that are linked together, for example, by disulfide linkages. The fragment may also comprise a multimolecular complex. A functional antibody fragment may typically comprise at least about 50 amino acids and more typically will comprise at least about 200 amino acids.

II. Determination of a Subject's Cancer Status

The present invention relates to the use of 5hmC to assess cancer status. More specifically, the 5hmC biomarker of the present invention can be used in diagnostic tests to determine the presence, absence, risk of, predict of, and/or progression of cancer in an individual, subject or patient. Other biomarkers known in the relevant art and other tests/assessments may be used in combination with the 5hmC biomarker described herein.

A. Kits for the Detection of 5hmC

In another aspect, the present invention provides kits for qualifying cancer status, i.e., diagnosing cancer, prognosing risk thereof, assessing treatment progression, etc., which kits are used to detect or measure the 5hmC biomarker status described herein. Such kits can comprise an affinity reagent (e.g., an antibody, aptamer, etc.) that binds to 5hmC and at least one reagent for detection thereof. The kits can further provide solid supports in the form of an assay apparatus that is adapted to use in the assay. Other materials useful in the performance of the assays can also be included in the kits, including test tubes, transfer pipettes, and the like. The kits can also include written instructions for the use of one or more of these reagents in any of the assays described herein.

Affinity reagents (e.g., antibodies, aptamers, etc.) to 5hmC may be included to provide concentrations from about 0.1 µg/mL to about 500 µg/mL, from about 0.1 µg/mL to about 50 µg/mL or from about 1 µg/mL to about 5 µg/mL or any value within the stated ranges. The kit may also include one or more buffers, such as a nuclease buffer or a hybridization/binding buffer. The kits can further include HCL and/or pretreatment buffers (e.g., citrate buffer, EDTA, and the like). Labels for the affinity reagents can also be included, along with instructions for labeling the reagents prior to use.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. However, various combinations of components may be comprised in a vial or similar container. The kits of the present invention also will typically include a means for containing the detection reagents, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 micrograms or at least or at most those amounts of dried dye are provided in kits of the invention. The dye may be re-suspended in any suitable solvent.

Kits may also include components that preserve or maintain the compositions that protect against their degradation. Such kits generally will comprise, in suitable means, distinct containers for each individual reagent or solution.

In certain embodiments, the methods of the present invention can also include detecting and/or quantitating control or reference proteins. Detecting and/or quantitating the reference proteins in the samples normalizes the results and thus provides further assurance that the assay is working properly. In a specific embodiment, affinity reagents specific for one or more reference proteins are included. Such reference proteins can include 5-methylcytosine (5mC), p63 (TP63), cytokeratin 1 (KRT1), cytokeratin 5 (KRTS), cytokeratin 8 (KRT8), cytokeratin 10 (KRT10), cytokeratin 14 (KRT14), cytokeratin 15 (KRT15), cytokeratin 18 (KRT18), Alpha-Methylacyl-CoA-Racemase (AMACR), CD34, CD38, beta-actin (ACTB), and glyceraldehyde-3-phosphate dehydrogenase (GAPDH) as positive controls while negative controls can include large ribosomal protein (RPLPO) and/or transferrin receptor (TRFC). In other embodiments, cells can be counterstained with, for example, DAPI or hematoxylin, and 5hmC can be normalized thereto.

The present invention further comprises a kit containing reagents for conducting an IHC analysis of tissue samples or cells from individuals, e.g., patients, including affinity reagents specific for 5hmC and, in some embodiments, for any reference proteins. In embodiments in which the affinity reagents are antibodies, such antibodies are readily available or can be prepared using well-established techniques. Antibodies specific for a biomarker described herein can be obtained, for example, from Active Motif, Diagenode, Millipore, Zymo Research, EpiGenie, Creative-diagnostics, Dake, Ventana, Cell Signaling Technology, Inc., Santa Cruz Biotechnology, Inc. or Abcam. The antibodies are preferably tagged with means for detecting the binding of the antibodies to the proteins of interest, e.g., detectable labels. Preferred detectable labels include fluorescent compounds, quantum dots or peroxidases (e.g., horseradish peroxidase (HRP));

however other types of detectable labels may be used. Detectable labels for antibodies are commercially available.

Immunohistochemical methods for detecting and quantitating in tissue samples are well known. Any method that permits the determination of 5hmC can be used. Such methods can be efficiently carried out using automated instruments designed for immunohistochemical (IHC) analysis. Instruments for rapidly performing such assays are commercially available, e.g., from Ventana Molecular Discovery Systems or Lab Vision Corporation. Methods according to the present invention using such instruments are carried out according to the manufacturer's instructions. Quantitation of 5hmC levels can be accomplished using any fluorescence quantification system including, but not limited to, the Telometer software application (http://demarzolab.pathology.jhmi.edu/telometer/) and the Isis Fluorescence Imaging System (MetaSystems Group, Inc. (Waltham, Mass.)).

III. 5hmC Antibodies

In one aspect, the present invention provides antibodies that specifically bind 5hmC that are useful for diagnostic or screening purposes. In certain embodiments, the antibodies described herein are isolated. In certain embodiments, the antibodies described herein are substantially pure.

In some embodiments the antibodies are monoclonal antibodies. In certain embodiments, the antibodies are chimeric, humanized, or human antibodies. The invention further provides bispecific antibodies. In certain embodiments, the antibodies are antibody fragments, such as Fab fragments.

In particular embodiments, the present invention provides isolated antibodies against 5hmC. The antibody, or antibody fragment thereof, can be any monoclonal or polyclonal antibody that specifically recognizes 5hmC. In some embodiments, the present invention provides monoclonal antibodies, or fragments thereof, that specifically bind to 5hmC. In some embodiments, the monoclonal antibodies, or fragments thereof, are chimeric or humanized antibodies that specifically bind to 5hmC or an eptiope or antigenic determinant thereof.

The antibodies against 5hmC find use in the experimental and diagnostic methods described herein. In certain embodiments, the antibodies of the present invention are used to detect the expression of a 5hmC protein in biological samples such as, for example, a tissue, blood, plasma, serum, cerebrospinal fluid sample and the like. Tissue biopsies can be sectioned and 5hmC protein detected using, for example, immunofluorescence or immunohistochemistry.

Polyclonal antibodies can be prepared by any known method. Polyclonal antibodies can be raised by immunizing an animal (e.g., a rabbit, rat, mouse, donkey, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

In some embodiments, of the present invention the monoclonal antibody against 5hmC is a humanized antibody. Humanized antibodies are antibodies that contain minimal sequences from non-human (e.g., murine) antibodies within the variable regions. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239:

1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments of the invention, it may be desirable to use an antibody fragment, rather than an intact antibody. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention further provides kits and articles of manufacture comprising one or more antibodies. In certain embodiments, the kits comprise at least two antibodies. In certain embodiments, the kits comprise at least one antibody that specifically binds a 5hmC protein.

IV. 5hmC Aptamers

The present invention relates to polynucleotide aptamers that specifically bind to 5hmC. In certain embodiments, the aptamers are used for 5hmC detection. Aptamer embodiments may be selected by any method known in the art. In one embodiment, aptamers may be selected by an iterative selection process such as Systemic Evolution of Ligands by Exponential Enrichment (SELEX). In this type of process, a random pool of oligonucleotides (e.g., about $10^5$ to about $10^{15}$ random oligonucleotides) is exposed to a target and the oligonucleotides that bind to the target are isolated and mutagenized and the process repeated until oligonucleotides that bind with the desired affinity to the target are identified.

In one embodiment of the invention, the aptamers are directed to 5hmC. In particular embodiments, the aptamers may bind 5hmC with a $K_d$ of less than about 1000 nM, e.g., less than about 500, 200, 100, 50, or 20 nM.

The length of the aptamers of the invention is not limited, but typical aptamers have a length of about 10 to about 100 nucleotides, e.g., about 20 to about 80 nucleotides, about 30 to about 50 nucleotides, or about 40 nucleotides. In certain embodiments, the aptamer may have additional nucleotides attached to the 5'- and/or 3' end. The additional nucleotides may be, e.g., part of primer sequences, restriction endonuclease sequences, or vector sequences useful for producing the aptamer.

The polynucleotide aptamers of the present invention may be comprised of, ribonucleotides only (RNA aptamers), deoxyribonucleotides only (DNA aptamers), or a combination of ribonucleotides and deoxyribonucleotides. The nucleotides may be naturally occurring nucleotides (e.g., ATP, TTP, GTP, CTP, UTP) or modified nucleotides. Modified nucleotides refers to nucleotides comprising bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific examples include 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. Modified nucleotides include labeled nucleotides such as radioactively, enzymatically, or chromogenically labeled nucleotides.

The aptamer may by synthesized by any method known to those of skill in the art. In one embodiment, aptamers may be produced by chemical synthesis of oligonucleotides and/or ligation of shorter oligonucleotides.

One aspect of the present invention relates to the use of the aptamers of the invention for diagnostic purposes. The aptamers can be used as binding agents in assays for measuring the level of 5hmC in a subject. Such measurements can be used to determine if 5hmC levels are abnormal relative to a control. Such measurements can further be used to diagnose a disease or disorder associated with 5hmC. The aptamers can be used for in vivo imaging or histological analysis. Numerous suitable binding assays are well known to those of skill in the art. Diagnostic assays can be carried out in vitro on isolated cells or cell lines for research purposes. Diagnostic assays can also be carried out on samples from a subject (e.g., tissue samples (biopsies, aspirates, scrapings, etc.) or body fluid samples (blood, plasma, serum, saliva, urine, cerebrospinal fluid, etc.)) or carried out in vivo. The aptamers can be labeled using methods and labels known in the art including, but not limited to, fluorescent, luminescent, phosphorescent, radioactive, and/or colorimetric compounds.

In one aspect, the invention relates to a method of measuring the level of 5hmC in a subject, comprising the step of using the polynucleotide aptamer to bind 5hmC. In another aspect, the invention relates to a method of diagnosing a disease or disorder associated with 5hmC in a subject, comprising the step of measuring the level of 5hmC in the subject using a polynucleotide aptamer. The level of 5hmC can then be correlated with the presence or absence of a disease or disorder associated with 5hmC.

For each of the methods described above, the methods may be carried out using a single aptamer targeted to 5hmC. In another embodiment, the methods may be carried out using two or more different aptamers targeted to 5hmC, e.g., three, four, five, or six different aptamers.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Sample Materials.

Mouse embryo tissue was obtained from seventeen day-old C57BL embryos. All remaining normal adult mouse tissues were from 11 week old FVB mice. All tissues were fixed in 10% buffered formalin immediately after tissue harvest and were embedded into paraffin. Tissue microarrays containing normal and tumor tissue form prostate, breast and colon were constructed at the Johns Hopkins TMA core facility.

Pathological Evaluation.

Samples were assessed by using an H-score system obtained by multiplying the intensity of the stain (0: no staining; 1: weak staining; 2: moderate staining; 3: intense staining) by the percentage (0 to 100) of cells showing that staining intensity (H-score range, 0 to 300). Only nuclear staining in epithelial cells was evaluated, either in tumor or benign tissues. Since nuclear 5hmC staining was robustly detected in stromal cells associated with tumor or benign tissue, only samples with strong stromal staining were evaluated as a means of censoring tissue samples that did not stain for 5hmC due to fixation or other artifacts.

Immunolabeling of 5hmC and 5mC.

To generate positive controls for 5hmC staining optimization, HEK293 cells were transiently transfected with myc-tagged TET2 constructs (obtained from Dr. Ari Melnick) or vector controls using Lipofectamine 2000 (Invitrogen, Carlsbad, Calif.). Cell pellets were fixed in 10% buffered formalin and embedded in paraffin as described previously. 5 micron paraffin sections were de-waxed and rehydrated following standard protocols. Antigen retrieval consisted of steaming for 30 min in citrate buffer (pH 6.0) followed by incubation in 3.5 N HCl for 15 min at room temperature. Slides were washed and equilibrated in TBS-Tween buffer (Sigma, St. Louis, Mo.) for 10 min. The same antigen retrieval was used for 5mC and 5hmC. For immunolabeling of 5hmC, the rabbit polyclonal 5 hydroxymethylcytosine specific antibody (Active Motif, Cat #39769, Carlsbad, Calif.) was applied at 1:20, 000 dilution. For 5mC detection, the mouse monoclonal 5 methylcytosine specific antibody (Calbiochem, EMD Chemicals Inc., San Diego, Calif.) was used at 1:2000 dilution. Both primary antibodies were incubated for 1 h at room temperature. Immuno-complexes were detected using the the PowerVision+™ immunohistochemistry detection system from ImmunoVision Technologies Co (Norwell, Mass., USA) with 3,3'-diaminobenzidine tetrahydrochloride (DAB) as the chromogen. After immunohistochemical staining, tissue sections were counterstained with hematoxylin. For immunofluorescence analysis, slides were pretreated as outlined above and incubated with rabbit polyclonal 5hmC specific antibody (Active Motif, Cat #39769) at a 1:8000 dilution with or without mouse monoclonal antibodies specific to myc (9E11, Santa Cruz, Calif.), cytokeratin 34βE12-903 (ENZO, Farmingdale, N.Y.) or cytokeratin 15 (Ab-1, NeoMarkers, Fremont, Calif.) at 1:50 dilutions Immuno-complexes were further labeled with secondary antibodies conjugated with Alexa 488 or Alexa 568 dyes (Invitrogen) and DNA was counterstained with DAPI. Slides were then visualized using a Nikon E400 fluorescence microscope (Nikon Instruments, Melville, N.Y.). To quantitate 5hmC levels in different cell compartments, representative images of 5hmC and 903 or CK15 co-labeled slides were analyzed using the Telometer software application. Therefore, signal intensities of individual cell nuclei in the basal and luminal/apical cell compartment were determined. To account for differences in overall DNA content, 5hmC signal intensities were normalized to DAPI intensities.

Isolation of Hematopoietic Cells.

Hematopoietic stem and progenitor cells were isolated as described previously. In brief, bone marrow samples were obtained from healthy individuals and mononuclear cells were isolated from fresh samples by Ficoll-Paque density centrifugation. To enrich for CD34 positive cell populations, cells were selected by Miltenyi Biotec columns (Auburn, Calif.). CD34 negative cells were spotted on glass slides. Aldehyde Dehydrogenase (ALDH) activity was assessed in CD34 positive cells by staining with Aldefluor (Aldagen, Durham, D.C.). Cells were further immunolabeled with anti-CD34 and anti-CD38 antibodies, sorted into CD34+CD38−ALDHhigh and CD34+CD38+ fractions and directly spotted on microscope slides. Samples were then stained with 5hmC specific antibodies.

Results

Development and Validation of an Immunohistochemical Staining Method for Global Analysis of 5hmC Levels In Situ.

Figures 6A, 6B, 6C, 6D, 6E, 6F:
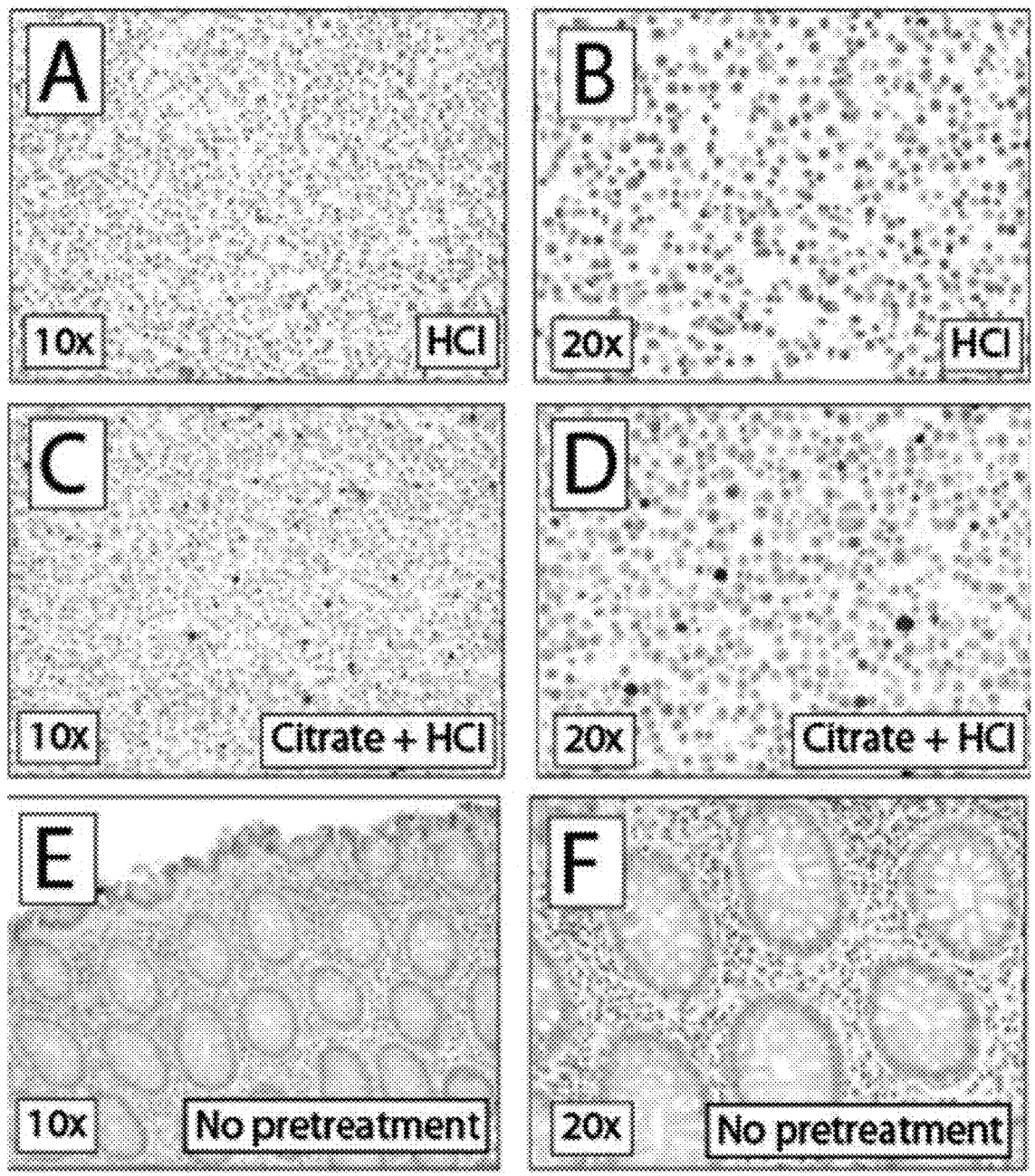
FIG. 6. Adequate antigen retrieval is necessary to obtain robust immunolabeling of 5hmC in formalin-fixed paraffin-embedded tissue sections. HEK293 cells transiently transfected with TET2 were fixed in formalin and embedded in paraffin. Tissue sections were either pretreated in 3.5 N HCl for 15 min alone (A, B) or steamed in citrate buffer (pH 6) for 30 min and then incubated in HCl (C, D). Slides were then stained with 5hmC specific antibodies and immunoreactive complexes were visualized with DAB. Note that pretreatment with HCl alone showed only faint staining, whereas the combination pretreatment of citrate steaming and HCl incubation showed robust labeling of 5hmC. Similarly, formalin-fixed paraffin-embedded sections of normal colon mucosa exhibited no 5hmC staining (E, F) when all pretreatment steps were omitted. Likewise, citrate steaming (G, H) or HCl treatment (I, J) alone did not result in 5hmC labeling. However, a combination of citrate steaming and HCl pretreatment resulted in efficient immunolabeling of 5hmC in normal human colon mucosa.
Figures 6G, 6H, 6I, 6J, 6K, 6L:
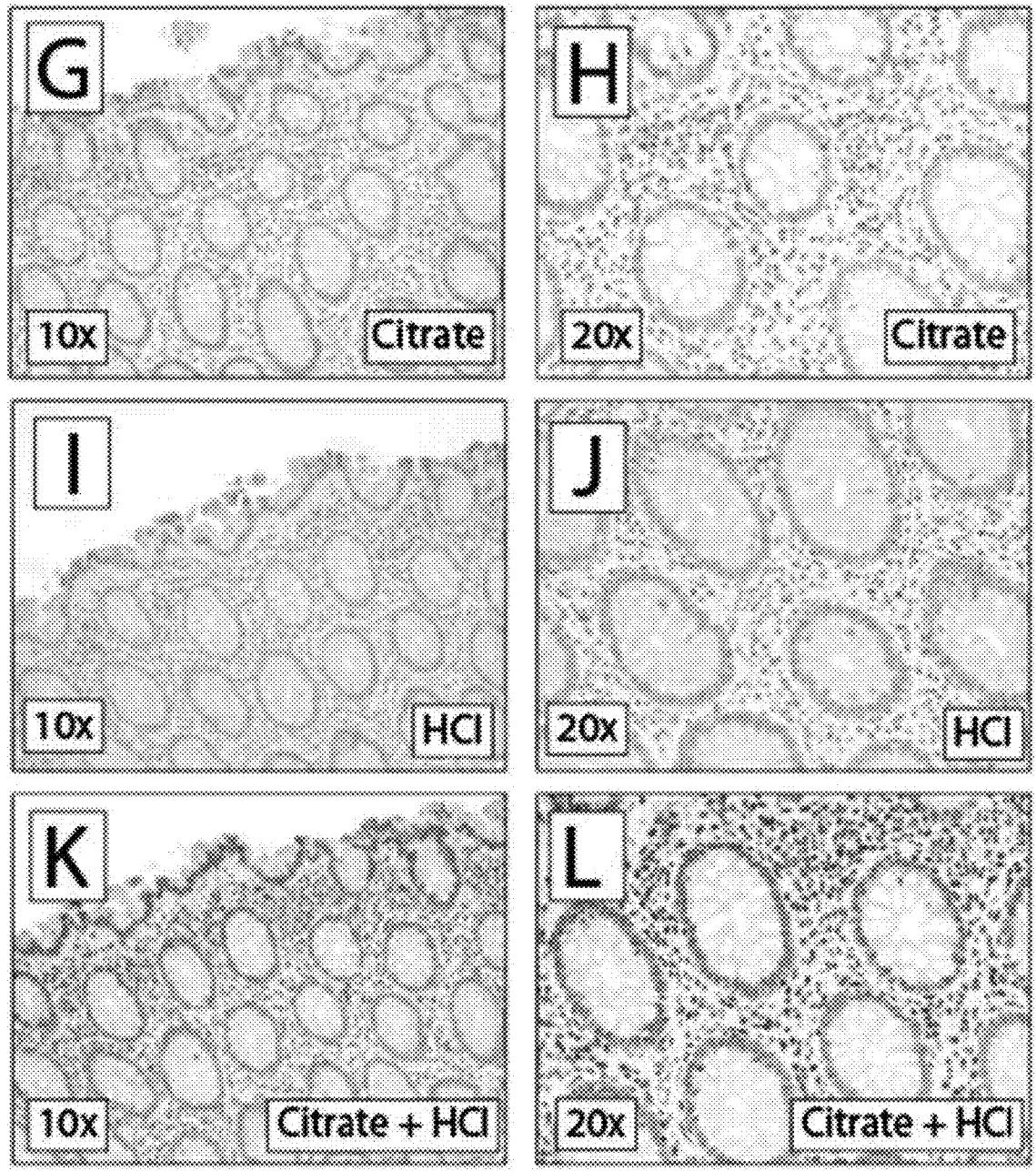

Investigation of tissue-specific 5hmC distribution has so far been attempted by using quantitative mass spectrometry based methods or semi-quantitative antibody-based immunofluorescence microscopy. Unfortunately, global 5hmC detection methods involving processing of tissue lysates do not allow the evaluation of 5hmC levels on a cell-by-cell basis Immunofluorescence microscopy, on the other hand, does not allow full morphological evaluation of the tissue and is often confounded by auto-fluorescence background, complicating interpretation. We therefore aimed to develop a method that allows the immunolabeling of 5hmC with a commercially available and recently extensively validated polyclonal antibody and subsequent immunohistochemical detection. To evaluate the specificity of the antibody, HEK293 cells were transiently transfected with expression vectors encoding myc-tagged TET2 or control (FIG. 1). Cells were fixed in 10% buffered formalin and embedded in paraffin as described previously. Sections of the obtained cell block were then double-immunolabeled with 5hmC and myc-tag specific antibodies. As shown previously, cells expressing TET2 (arrowheads) showed strong nuclear 5hmC staining providing a robust positive control for staining optimization (FIG. 1 A, B, C). Conversely, HEK293 not expressing TET2myc and control HEK293 cells did not exhibit strong staining for 5hmC. Next, TET2 expressing and control HEK293 cells were incubated with 5hmC antibodies; immunocomplexes were visualized using HRP conjugated secondary antibodies with DAB as a chromogen. Cells expressing TET2 showed a strong nuclear signal for 5hmC, whereas control transected cells only showed very faint to undetectable nuclear staining. The low intensity of staining in the control cells likely reflects the low levels of 5hmC previously observed in HEK293 cells. Our pretreatment protocol included two antigen retrieval steps: a 30 min steaming in citrate buffer (pH 6.0) and a 15 min incubation in 3.5 N HCl. Both steps were required for efficient immunolabeling of 5hmC in formalin-fixed paraffin-embedded material; omission of the citrate steam and/or HCl steps resulted in almost complete absence of 5hmC staining (FIG. 6), highlighting the importance of adequate antigen unmasking for immunohistochemical analysis.

Distribution of 5hmC Content in Mouse Embryonic Tissues.

We first determined the 5hmC staining pattern in the developing mouse embryo. Seventeen-day-old mouse embryos were fixed, paraffin-embedded, and processed as outlined below. In line with recent reports, we detected significant levels of 5hmC in the mouse cerebral cortex and cerebellum. In addition, 5hmC was also detectable in the majority of tissues throughout the mouse embryo. Interestingly, we observed a strong association of 5hmC content with the differentiation state of cells in many hierarchically organized tissues. For instance, in the intestine of the embryo, cells lining the crypts of the mucosa showed almost no staining for 5hmC, whereas more apical cells exhibited strong staining (FIG. 2A). Similarly, the skin in the developing mouse embryo also showed a hierarchical distribution of 5hmC staining, with cells in the basal epithelial layer showing very low staining intensities and more apical cells staining strongly for 5hmC (FIG. 2B). These patterns suggest that in the developing embryo, 5hmC is more abundant in more differentiated cell compartments than in the less differentiated cell compartments.

5hmC Content is Generally Correlated with Differentiation State of Cells in Hierarchically Organized Mouse and Human Adult Tissues.

Figure 2:
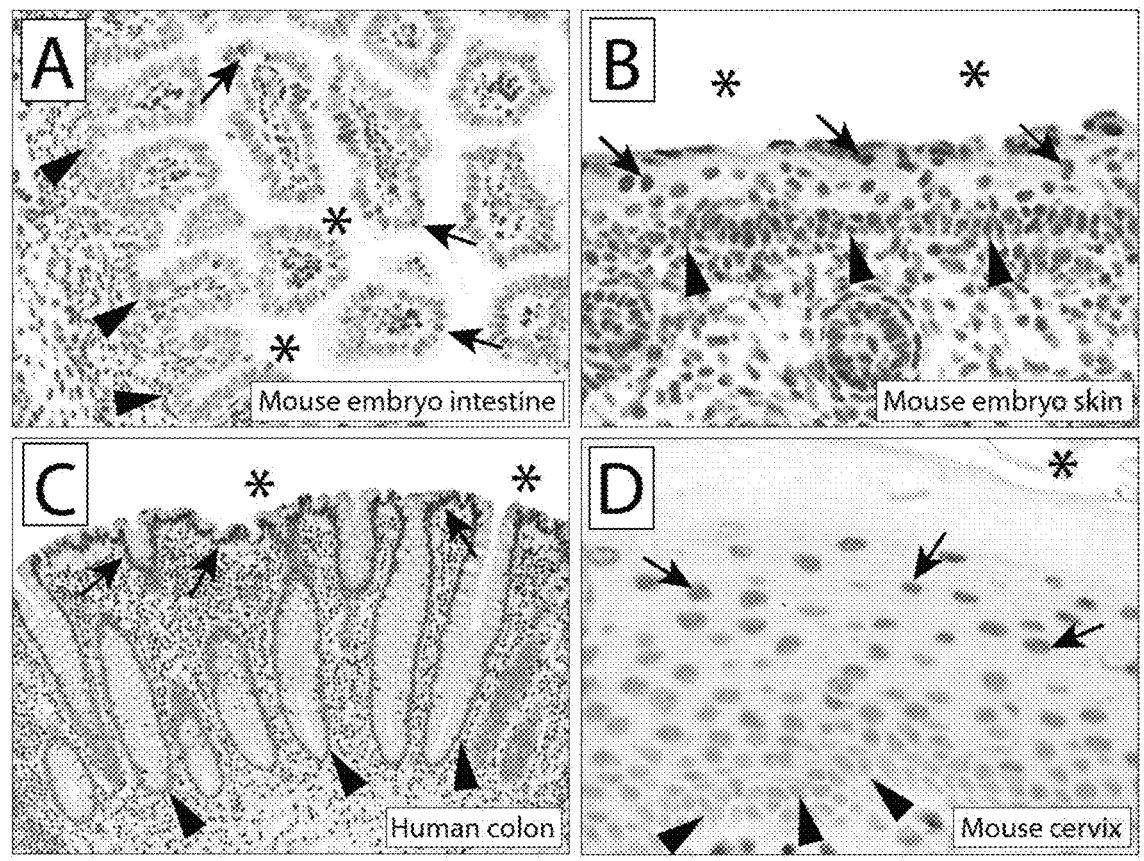
FIG. 2: 5hmC is abundant in embryonal and adult tissues, with differential abundance in basal vs. luminal cell compartments of stratified epithelia. Micrographs show 5hmC staining in the intestine (A) and skin (B) of a 17 day old mouse embryo. Note the reduced staining of 5hmC staining in the basal cell compartment (indicated by arrowheads) compared to the luminal/apical epithelial cells (indicated by arrows). (C) Normal human adult colonic mucosa exhibits strong staining for 5hmC in apical epithelial cells (indicated by arrows); epithelial cells in the base of the crypt (indicated by arrowheads) show greatly reduced staining intensities. Note the strong 5hmC staining of associated stromal nuclei. (D) Hierarchical distribution of 5hmC staining in murine cervix. Asterisk (*) indicates apical/luminal surface.
Figure 7:
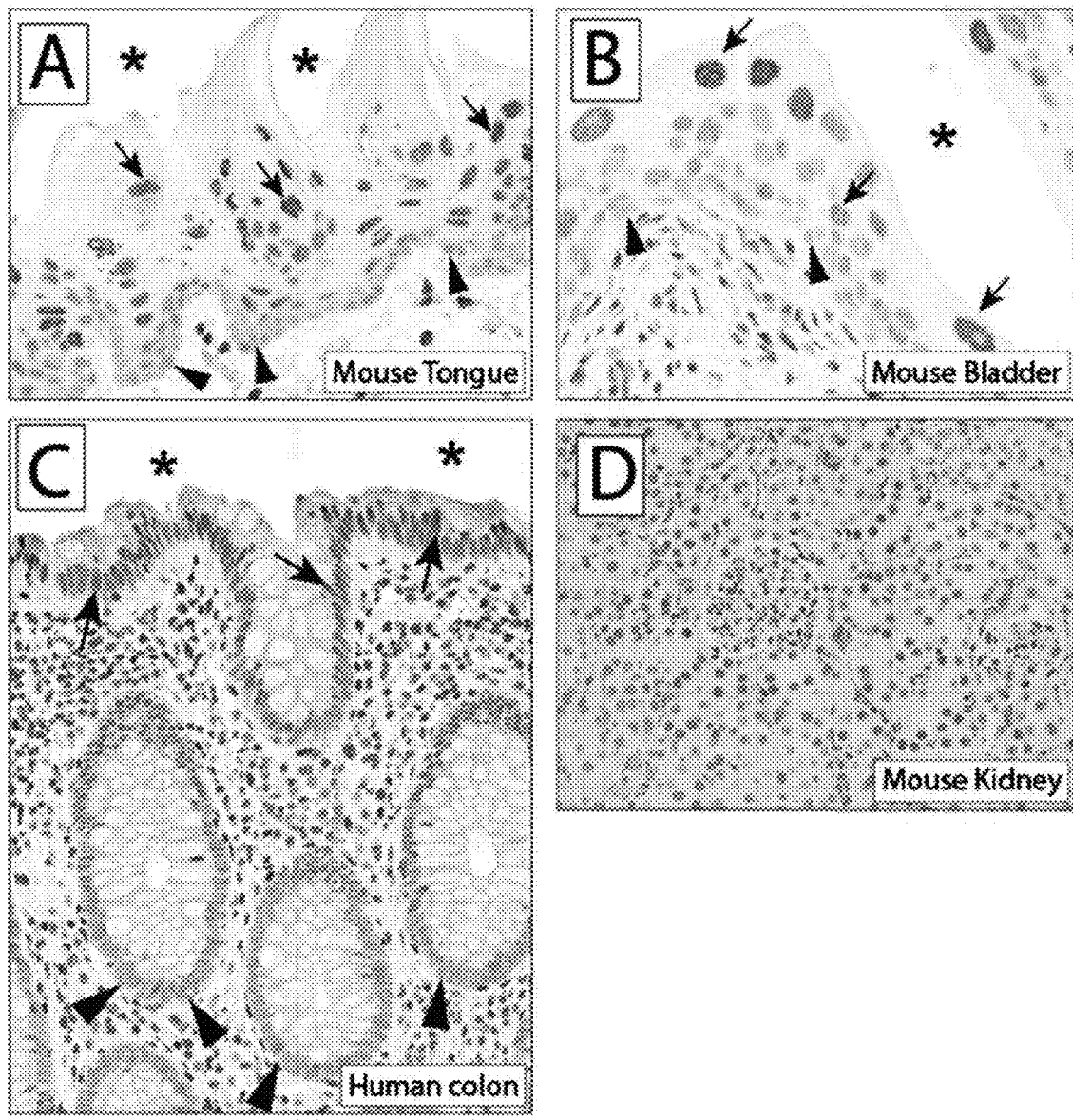
FIG. 7. 5hmC staining in different human and mouse tissue types. Across multiple stratified epithelial tissues, apical epithelial cells exhibited strong staining for 5hmC (indicated by arrows), whereas the basal epithelial compartment showed much weaker 5hmC staining (indicated by arrowheads), as shown for the cornified epithelia of murine tongue (A), transitional epithelium from mouse bladder (B), the stratified epithelium of the human colon (C). Murine kidney (D) tissue showed strong immunoreactivity for 5hmC in the majority of cell nuclei. Asterisks (*) indicate the location of the lumen.

To test whether this association of 5hmC with differentiation in hierarchically organized tissues would also be maintained in adult tissues, we investigated several tissue types from adult mice and humans. Human colon represents a classical model for hierarchical tissue differentiation. Cells at the base of the colonic crypt proliferate and represent the regenerative tissue stem/progenitor cell compartment. Conversely, cells in the luminal side of the colon form the terminally differentiated cell compartment. Interestingly, we found that this hierarchical differentiation is associated with strong differences in 5hmC levels. Whereas apical cells of the colonic mucosa show strong 5hmC staining, cells in the base of the crypts had greatly reduced 5hmC levels (FIG. 2C). Other stratified epithelia, including that in cervix, oral mucosa, and bladder, exhibited a similar distribution of 5hmC staining in which apical cells showed higher 5hmC levels as compared to basal cells (FIG. 2, FIG. 7).

Figure 3:
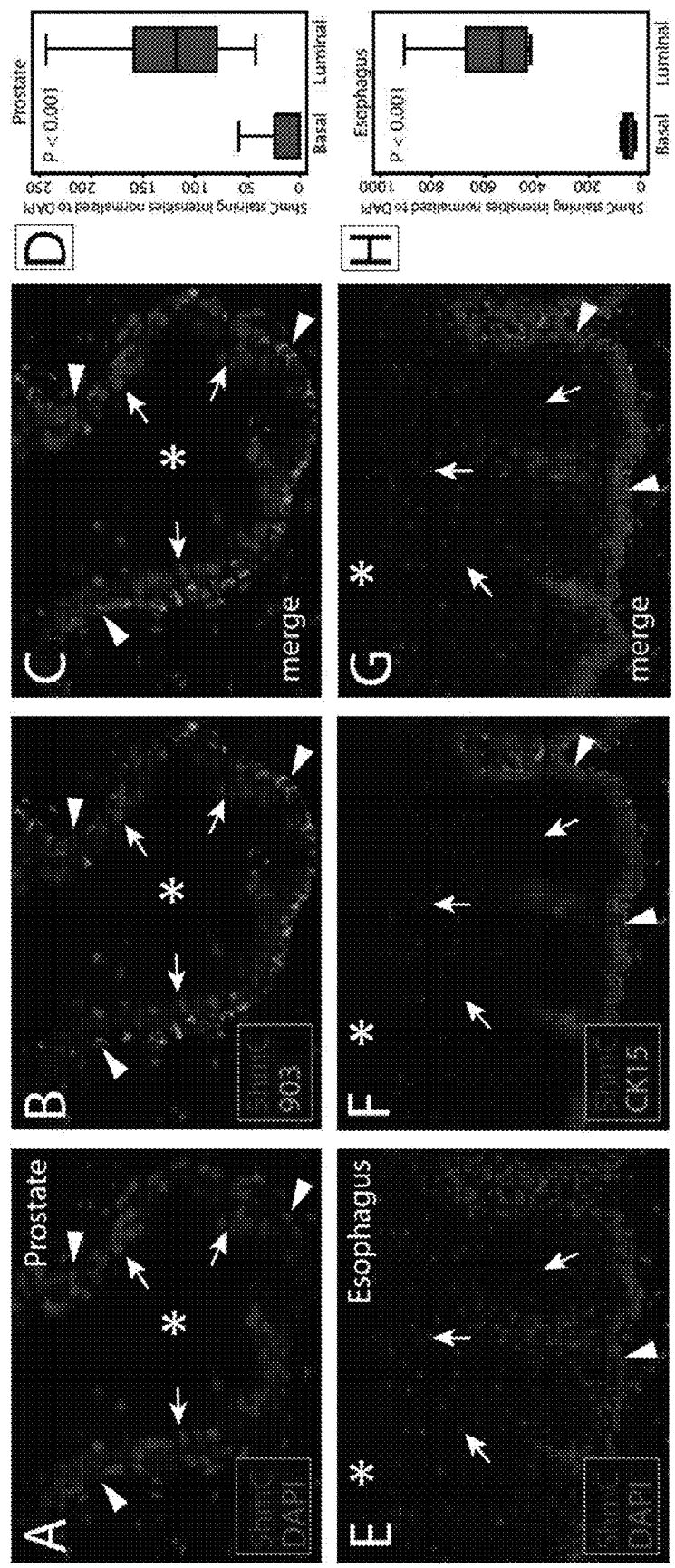
FIG. 3: Quantitative analysis of the hierarchical distribution of 5hmC in stratified epithelia. (A-C) Representative micrographs of normal prostate epithelia co-immunolabeled for 5hmC (red) and basal cell specific cytokeratin 903 (green). Nuclei were counterstained with DAPI (blue). (D) Box-plots show the distribution of 5hmC fluorescence intensities in basal (903+) and luminal (903−) cells, normalized to DAPI. (E-G) Representative micrographs of normal esophageal mucosa co-immunolabeled for 5hmC (red) and basal cell specific CK15 (green). (H) Distribution of 5hmC staining intensities in basal (CK15+) and luminal (CK15−) cells, normalized to DAPI. Arrowheads indicate basal cells, arrows indicate luminal cells, Asterisks (*) indicate lumen.

To assess this differential distribution more rigorously and quantitate 5hmC levels in luminal and basal cell compartments, we used immunofluorescence microscopy coupled with quantitative image analysis. Slides containing normal human prostate or normal human esophagus were co-immunolabeled with 5hmC antibodies and basal cell specific cytokeratin antibodies (34βE12-903 for prostate, CK15 for esophagus). Signal intensities of 5hmC were determined in basal and luminal/apical cell compartments (FIG. 3) using quantitative image analysis software. We observed a statistically significant difference in 5hmC staining intensities between basal and luminal cells for prostate (median signal intensity values: basal 0, luminal 118, p<0.0001) and esophageal epithelia (median signal intensity values: basal 53.6, luminal 555.2, p<0.0001) providing a quantitative validation of the differential distribution of 5hmC in these tissues (FIG. 3).

5hmC Levels are Reduced in Hematopoietic Stem and Progenitor Cells Compared to More Differentiated Counterparts.

Figure 4:
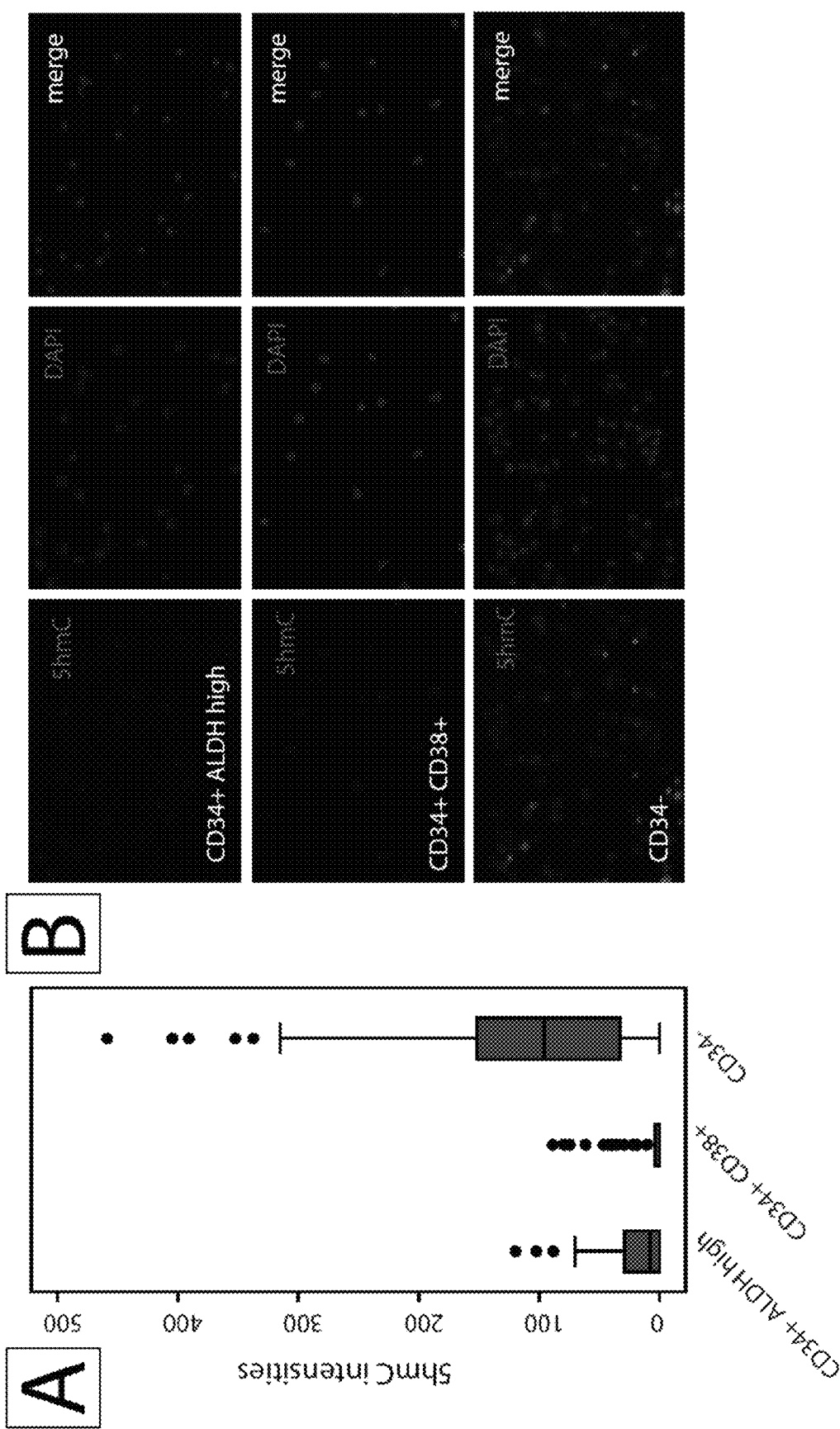
FIG. 4: Quantitative analysis of the hierarchical distribution of 5hmC in hematopoietic cells. Ficoll-Paque enriched, CD34-depleted bone marrow, or FACS sorted CD34+; CD38−;ALDH-high hematopoietic stem cells, or CD34+; CD38+ progenitor cells were spotted on glass slides, stained with 5hmC specific antibodies and visualized using immunofluorescence microscopy. Signal intensities were determined by quantitative image analysis. (A) Distribution of 5hmC signal intensities in the stem cell (CD34 positive ALDH high), progenitor cell (CD34, CD38 positive) and differentiated cell (CD34 negative) compartments. (B) Representative micrographs of each enriched fraction.
Figure 8:
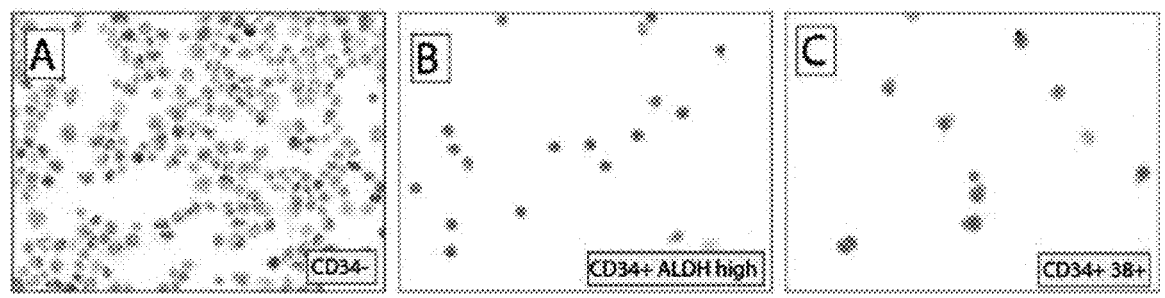
FIG. 8. 5hmC levels are low in hematopoietic stem/progenitor cells. 5hmC immunohistochemical staining in (A) Ficoll-Paque enriched, CD34-depleted bone marrow, (B) CD34+CD38−ALDHhigh hematopoietic stem cells and (C) CD34+CD38+ progenitor cells. Bone Marrow samples were obtained from healthy individuals and mononuclear cells were isolated from fresh samples by Ficoll-Paque density centrifugation. To enrich for CD34+ cell populations, cells were selected by Miltenyi Biotec columns. ALDH1A1 activity was assessed in CD34+ cells by staining with Aldefluor. Cells were further immunolabeled with anti-CD34 and anti-CD38, sorted into CD34+CD38−ALDHhigh and CD34+CD38+ fractions and directly spotted on microscope slides. Samples were then stained with 5hmC specific antibodies. Representative micrographs of all 3 fractions are shown. Note that 5hmC staining is greatly reduced in the CD34+CD38− ALDHhigh (B) and CD34+CD38+ (C) cell populations.

Although not necessarily hierarchically organized by location of cell compartments, hematopoietic cells in the bone marrow show a distinct hierarchy of differentiation. Well-defined markers allow the cell compartment specific enrichment of undifferentiated stem cells, progenitor cells, and terminally differentiated mature blood cells. Using FACS, hematopoietic stem cells (CD34+;CD38−;ALDH+) and progenitor cells (CD34+;CD38+) were sorted as described previously. Cells were then stained with 5hmC specific antibodies and staining intensities in hematopoietic stem and progenitor cells were compared to more differentiated bone marrow cells that were depleted of CD34 positive cells (FIG. 4, FIG. 8). Consistent with what was observed for stratified epithelial tissues as described above, hematopoietic stem and progenitor cell populations exhibited much lower 5hmC content than their more differentiated CD34 negative counterparts (FIG. 4; $p<0.001$).

Loss of 5hmC in Human Cancers.

Figure 5:
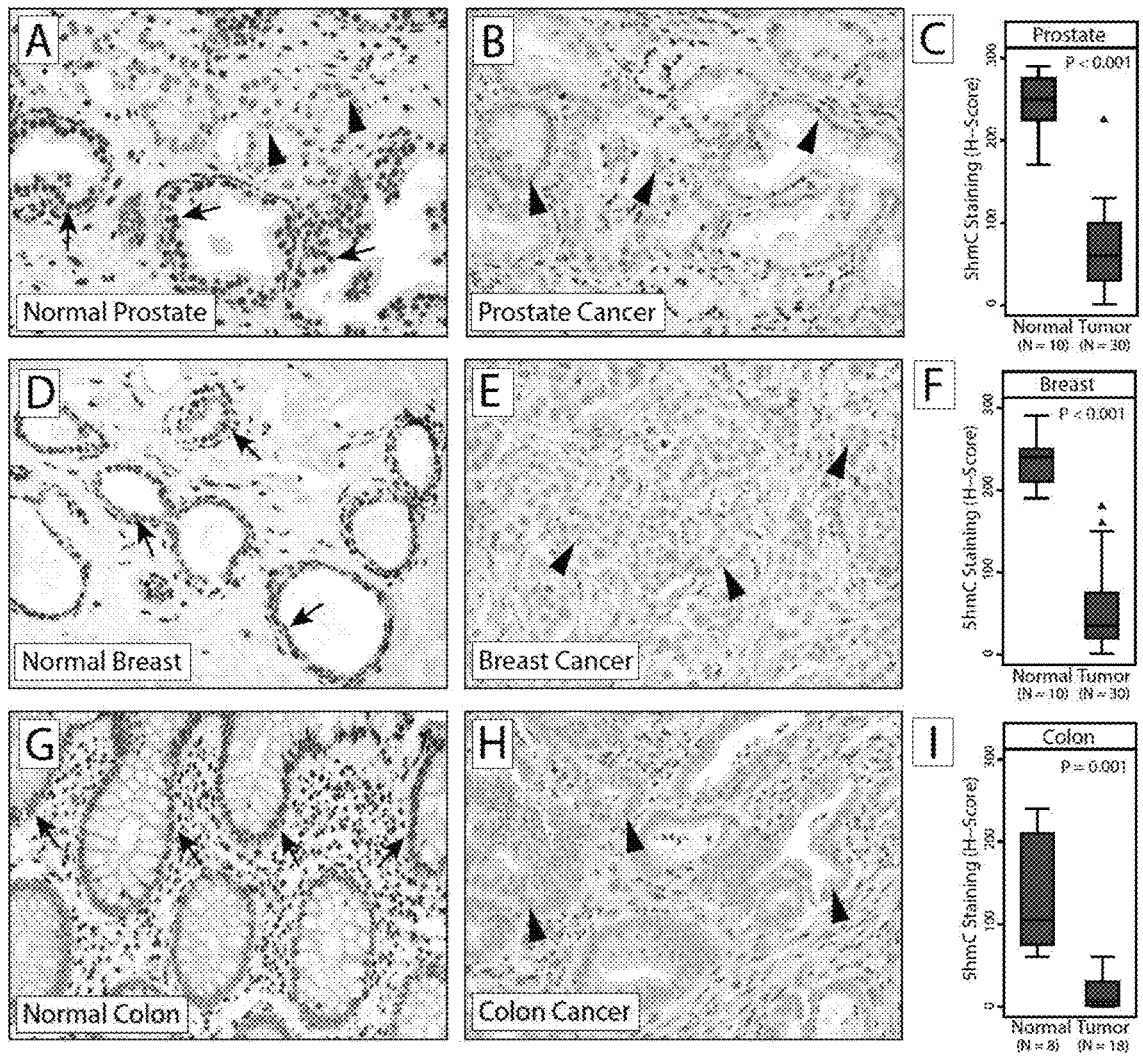
FIG. 5: Significant reduction in 5hmC levels in cancers. Micrographs of representative 5hmC staining in normal human prostate (A) and prostate adenocarcinoma (B), normal breast (D) and ductal breast cancer (E) and normal colon mucosa (G) and adenocarcinoma of the colon (H). (C, F, I) show distributions of semi-quantitative intensities scores in normal and tumor cells in box-and-whisker plots. Note that (A) contains a small focus of cancerous glands (indicated by arrowheads) infiltrating normal prostatic epithelium. Arrows indicate normal epithelial cells; arrowheads show tumor cell nuclei with reduced 5hmC staining.

Tumors often adopt a caricaturized differentiation phenotype consisting of loss of some features of differentiation and gain of certain functions, such as self renewal, that are more characteristic of less differentiated stem cells; these changes are nearly universally associated with profound epigenetic alterations. We assessed whether tumor cells have 5hmC contents closer to terminally differentiated cells or to tissue stem cell compartments from their tissue of origin. To determine the levels and distribution of 5hmC in cancer and normal tissues, we assessed a total of 78 carcinoma and 28 normal tissue samples from prostate, breast, and colon (FIG. 5). Analysis of this set of normal tissues confirmed the general pattern of increased 5hmC content in more differentiated cell types in the normal prostate and colon; terminally differentiated luminal cells in these tissues showed much stronger 5hmC staining than basal cells, the likely compartment containing the tissue stem/progenitor cells (FIG. 5A,G). In breast tissue, the identity of the undifferentiated tissue stem cell compartment is more controversial. We observed that the myoepithelial cells in normal breast glands tended to show a subtle, but noticeable, stronger 5hmC staining than the normal luminal cells. Nonetheless, comparing these normal tissues to cancers arising from the same tissues, we observed a profound reduction in 5hmC content in the cancers for all three tumor types ($p<0.001$ for prostate and breast; $p=0.001$ for colon). Interestingly, in prostate tissues, where we could observe normal prostate glands adjacent to malignant glands, we saw a significant reduction in 5hmC staining in the cancerous glands compared to the adjacent normal glands (FIG. 5A arrowheads). 5hmC staining intensities were not associated with clinicopathological features such as grade and stage. Even small lesions of low histological grade showed profound reduction of 5hmC. This suggests that the global loss of 5hmC could be an early event in carcinogenesis.

Figures 9A, 9B:
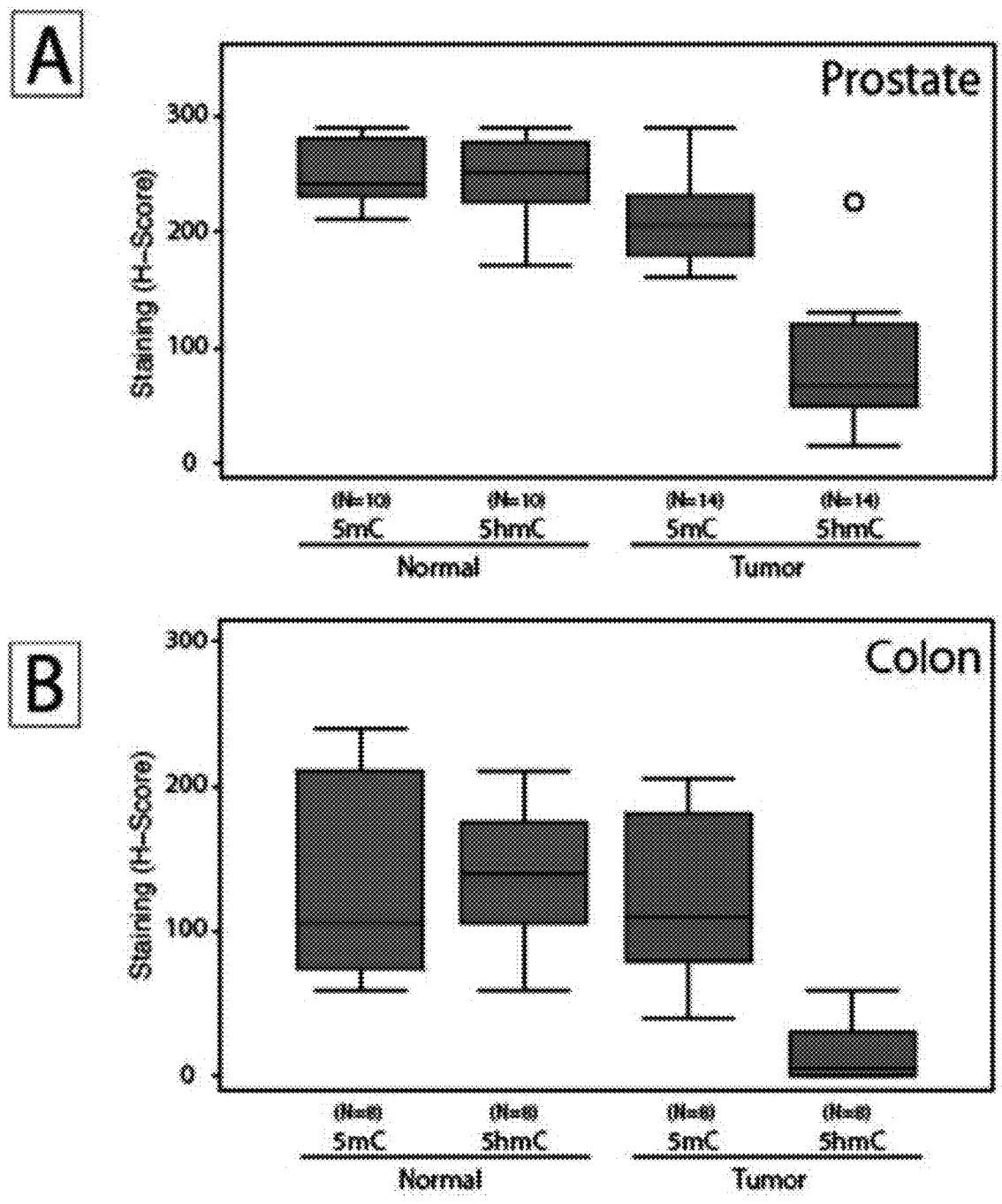
FIG. 9. Decrease of 5hmC is independent of 5mC. To assess if loss of 5hmC in cancers is accompanied by decreased 5mC levels, normal and tumor tissue of prostate (A) and colon (B) were stained with 5hmC and 5mC specific antibodies and staining intensities and distribution of 5mC and 5hmC was assessed semi quantitatively using the H-score system. Whereas 5hmC levels were profoundly reduced in prostate and colon adenocarcinoma, global 5mC levels were only modestly decreased. No correlation between 5hmC and 5mC staining was observed. (C, D) Representative micrographs of adjacent sections showing greatly decreased 5hmC staining in prostate cancer cells (C, arrowheads) but no reduction in 5mC staining (D). Note that normal luminal cells (arrows) show strong staining for 5hmC and 5mC.
Figures 9C, 9D:
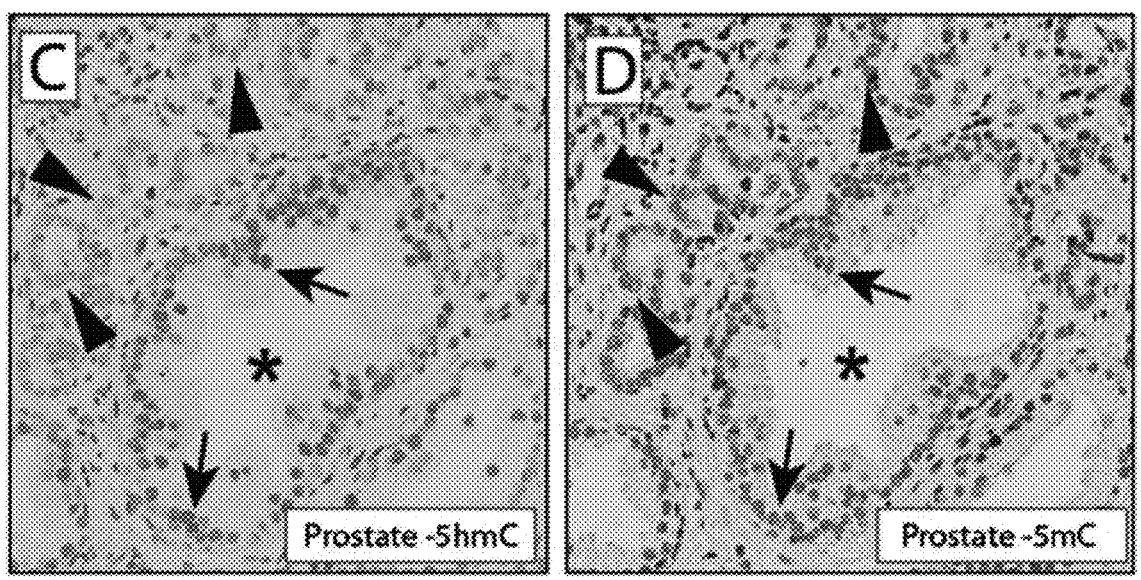

Since 5mC is the substrate for the TET-enzyme mediated conversion to 5hmC, the global loss of 5hmC seen here could simply reflect a decrease in 5mC levels, which is known to occur in human cancers. Therefore, we assessed 5mC levels in normal and tumor tissues from the colon and the prostate using a previously validated immunohistochemical staining method that specifically detects 5mC (FIG. 9). As compared to normal tissue, adenocarcinoma of the colon and the prostate only showed a very modest decrease in 5mC intensities (FIG. 9), and we observed no correlation between 5hmC and 5mC. These data suggest that the global decrease of 5mC cannot alone account for the profound loss of 5hmC levels in solid tumors.

Discussion

The recent finding that oxidation of 5mC to 5hmC by enzymes of the ten-eleven translocated (TET) family occurs in mammalian genomes has raised many questions regarding the role of this DNA modification in epigenetic regulation. Even though several studies have investigated the complex role of TET proteins and 5hmC in embryonic stem cell biology, the relevance of this mark in developing normal and adult tissues remained essentially unexplored.

Here, we developed a novel, robust immunohistochemical detection method for 5hmC and used this method to detect 5hmC in a large number of murine and human tissues. Interestingly, we found that hierarchically organized epithelia as well as hematopoietic cells in the bone marrow show a differentiation-dependent 5hmC distribution. Cells in the colonic crypt, basal cells of the prostate, as well as hematopoietic stem/progenitor cells exhibited greatly reduced 5hmC levels compared to more differentiated counterparts, suggesting that adult tissue stem/progenitor cells across a broad range of tissue types might be characterized by low 5hmC levels. Differentiation and maturation conversely appeared to be associated with an increase in 5hmC. Based on these data, we can hypothesize that accumulation of 5hmC in the genome is involved in differentiation of tissue stem/progenitor cells. This hypothesis is supported by recent reports showing that genetic disruption of TET2 in hematopoietic cells could lead to increased hematopoietic stem cell self-renewal, accumulation of hematopoietic stem/progenitor cells, and reduced differentiation of hematopoietic stem cells.

This observation is somewhat in contrast to recent reports from murine embryonic stem cells, where the differentiation of embryonic stem cells appeared to be associated with a loss in 5hmC. These discrepancies could reflect differences in the biology between embryonic and tissue stem cells and could point to a differential role of 5hmC in very early development versus later development and adult tissue development/differentiation.

Recent reports on the detection of 5hmC in adult tissues have been somewhat conflicting. One explanation for these variable results is certainly the use of different detection methods. In this study, we noted that robust immunohistochemical detection of 5hmC from formalin-fixed paraffin-embedded tissue requires specific antigen retrieval. Omission of these antigen retrieval steps led to vastly different results (FIG. 6) and, therefore, explained some of the prevailing discrepancies in the literature.

The functional role of 5hmC in regulating differentiation and epigenetic states of adult tissues remains unknown. It has been proposed that 5hmC cannot be bound by methyl-binding domain proteins such as MeCP2, MBD1, and MBD2, which are known to associate with 5mC and recruit the chromatin repression complex. Accumulation of 5hmC could therefore have a significant impact on gene expression states. Moreover, it was suggested that 5hmC is not recognized by the DNA methylation maintenance machinery, suggesting that the presence of 5hmC could lead to a passive loss of DNA methylation during cell division. Most interestingly however, the conversion of 5mC to 5hmC could also represent a mechanism for active demethylation. In a process that involves activation induced deaminase (AID) and base excision repair, 5hmC can be converted to cytosine, providing a mechanism for the sequential, active conversion of 5mC to cytosine. Such a process provides an interesting mechanism for plasticity of DNA methylation marks.

Our observation that 5hmC levels are significantly reduced in three different types of human carcinoma suggests that the loss of 5hmC could be a general feature of carcinogenesis. Indeed, in several hematological malignancies including AML and MDS, reduced 5hmC levels have been associated with mutations in the TET genes. However, it is unlikely that missense mutation in the TET enzymes can explain the almost universal reduction in 5hmC levels in colorectal, prostate and breast carcinoma, since large scale sequencing efforts have not identified TET family members as frequently mutated in these tumors. Recent evidence suggests that a large number of oxidizing enzymes, including the TET family, can be inhibited by oncogenic metabolites, such as 2-hydroxyglutarate. It is, therefore, possible that cancer specific metabolic perturbations can influence 5hmC levels and, consequently, alter the epigenetic makeup of a cell.

In many solid tumors, cancer progression is associated with a progressive loss of 5mC marks resulting in a global hypomethylation phenotype. Since 5mC is required as a substrate for oxidation to generate 5hmC, reduced 5mC levels could explain, at least partly, the decrease of 5hmC observed in tumors. To address a possible correlation between 5hmC and 5mC loss we stained a series of tumor and normal tissues from prostate and colon with an antibody that specifically recognizes 5mC (FIG. 9). Using this method, we observed only a modest reduction of global 5mC staining intensities between cancerous and normal tissue of the colon and prostate, which is in line with recent reports. Furthermore, we found no association between 5mC and 5hmC staining levels suggesting that the reduction in 5hmC can occur independently of reductions in 5mC.

In conclusion, our study identifies a hierarchical distribution of 5hmC levels in embryonic and adult tissues and provides evidence for a cancer-associated loss of 5hmC.

We claim:

1. A method for identifying a patient as having cancer comprising the steps of:
   a. providing a formalin-fixed, paraffin-embedded or fresh frozen sample from the patient tissue;
   b. steaming the sample in antigen retrieval buffer;
   c. incubating the sample in hydrochloric acid (HCl);
   d. incubating the sample with an affinity reagent specific for 5hmC under conditions to form a complex between the affinity reagent and 5-hydroxymethylcytosine (5hmC) present in the sample;
   e. detecting the complexes formed between 5hmC and the affinity reagent with secondary detection reagents;
   f. quantifying 5hmC levels; and
   g. identifying the patient as having cancer if the 5hmC levels in the sample are reduced as compared to a control.

2. The method of claim 1, wherein the patient sample is from any tissue with a suspected neoplastic growth.

3. The method of claim 2, wherein the neoplastic growth is a cancer from prostate, breast, colon or leukemia.

4. The method of claim 3, wherein the quantifying step is accomplished by semi-quantitative scoring or by using an image analysis software program.

5. A method for identifying a patient as having cancer comprising the steps of:
   a. providing a formalin-fixed, paraffin-embedded sample from the patient tissue;
   b. steaming the sample in citrate buffer;
   c. incubating the sample in hydrochloric acid (HCl);
   d. immunolabeling 5-hydroxymethylcytosine (5-hmC) with an antibody;
   e. detecting the immunocomplexes formed between 5-hmC and the antibody;
   f. quantifying 5-hmC levels; and
   g. identifying the patient as having cancer if the 5-hmC levels in the sample are reduced as compared to a control.

6. The method of claim 5, wherein the patient tissue is from the prostate, breast or colon.

7. The method of claim 5, wherein the detection step comprises labeling the immunocomplexes with secondary antibodies conjugated with a fluorescent dye and visualizing using a fluorescence microscope.

8. The method of claim 7, wherein the quantifying step is accomplished using an image analysis software program.

* * * * *